(12) United States Patent
Müller et al.

(10) Patent No.: US 8,708,318 B2
(45) Date of Patent: Apr. 29, 2014

(54) APPARATUS FOR INCREASING THE ATMOSPHERIC HUMIDITY OF AN OUTDOOR WEATHERING FACILITY

(76) Inventors: Hans-Willi Müller, Korschenbroich (DE); Hans-Peter Schlegelmilch, Mönchengladbach (DE)

( * ) Notice: Subject to any disclaimer, the term of this patent is extended or adjusted under 35 U.S.C. 154(b) by 282 days.

(21) Appl. No.: 13/125,037

(22) PCT Filed: Oct. 20, 2009

(86) PCT No.: PCT/EP2009/007486
§ 371 (c)(1),
(2), (4) Date: Oct. 11, 2011

(87) PCT Pub. No.: WO2010/046073
PCT Pub. Date: Apr. 29, 2010

(65) Prior Publication Data
US 2012/0018909 A1    Jan. 26, 2012

(30) Foreign Application Priority Data
Oct. 22, 2008  (EP) .................................... 08018468

(51) Int. Cl.
*B01F 3/04* (2006.01)

(52) U.S. Cl.
USPC ....................................... 261/112.1; 73/865.6

(58) Field of Classification Search
USPC .......................... 261/112.1, 84, 100; 73/865.6
See application file for complete search history.

(56) References Cited

U.S. PATENT DOCUMENTS

| | | | |
|---|---|---|---|
| 2,945,417 A | | 7/1960 | Coleman |
| 3,327,536 A | * | 6/1967 | Fitzgerald .................... 73/865.6 |
| 3,521,966 A | | 7/1970 | Archer |
| 4,807,247 A | * | 2/1989 | Robbins, III .................... 374/57 |

FOREIGN PATENT DOCUMENTS

| | | |
|---|---|---|
| DE | 202005000092 U1 | 5/2006 |
| FR | 790965 A | 11/1935 |

* cited by examiner

*Primary Examiner* — Robert A Hopkins
(74) *Attorney, Agent, or Firm* — Kilpatrick Townsend & Stockton LLP

(57) ABSTRACT

An apparatus for increasing the atmospheric humidity of an outdoor weathering facility for test samples in a test area (1), with a graduating unit (2) for controlling the level of the atmospheric humidity in the test area (1) by discharging an evaporated amount of fluid and with a device (4) for measuring the level of the atmospheric humidity over time during a test period.

10 Claims, 2 Drawing Sheets

APPARATUS FOR INCREASING THE ATMOSPHERIC HUMIDITY OF AN OUTDOOR WEATHERING FACILITY

The invention relates to an apparatus for increasing the atmospheric humidity of an outdoor weathering facility as claimed in claim 1.

It is known to expose materials to outdoor weathering in order to test their resistance to atmospheric influences under "real environmental conditions". The aging behavior of materials exposed to application of outdoor weathering is tested in an "outdoor test" in order to determine the influence of insolation, temperature, rain, humidity etc.

In the automobile industry, in particular, a component of the development of motor vehicles is testing them as a whole for their capability regarding different weather conditions. Apart from the paint and the external materials and/or coatings, the interior with the appropriate materials is tested for the weather conditions in the outdoor test. These result from the respective yearly seasons and from the climatic zones of the globe, which partly differ from one another extremely. A principle aspect is the influence of insolation on a motor vehicle, the aim being to determine the effects with regard to the influence of radiation and temperature.

The tests are carried out at different locations of the globe at outdoor weathering facilities with extreme weather conditions. The tests for the motor vehicle industry are carried out in order to obtain extreme climatic conditions in, for example, Florida and/or Kwazulu Natal (for wet hot climate) and Arizona and/or the Kalahari (for dry hot climate). Because of the fact that the outdoor weathering lasts in part for several years and is attended by the corresponding costs for the long trial period and transportation and logistics costs in order to bring the samples and/or motor vehicles into the appropriate climatic zones, special methods have been applied to shorten test times and have led to a reduced time period for the laboratory trials. The outdoor weathering conditions are reenacted and intensified and/or artificially increased.

DE 101 55 245 B4 discloses by way of example how to carry out weathering simulations in weathering chambers. A weathering chamber is subject in this case to an inherent disadvantage that the weathering can only be simulated, and that there are reservations with regard to such a simulation.

The shorter testing times desired for economic reasons are acquired through intensified and therefore unnatural loads on the samples or motor vehicles. The risk exists here that aging processes will be initiated that do not occur outdoors. It is not possible to dispense with a "real" outdoor weathering facility, since the most reliable statements and data relating to the resistance of the materials are obtained by the conditions, coming closest to the real ones, in outdoor weathering facilities, and subsequent testing of the respective properties.

It is an object of the invention to provide an apparatus for increasing the atmospheric humidity of an outdoor weathering facility that enables outdoor weathering to be carried out using a simplified testing possibility.

The object is achieved in accordance with the features of claim 1.

An apparatus is hereby provided for increasing the atmospheric humidity for outdoor weathering of test samples, in particular motor vehicles, in a test area. The apparatus has a graduating unit for controlling the level of the atmospheric humidity in the test area by discharging an evaporated amount of liquid. Furthermore, the apparatus comprises a device for measuring the level of the atmospheric humidity as a function of time during a test period. The apparatus can be used in a dry hot climate to simulate a wet hot climate that corresponds substantially to the natural properties of a wet hot climate. The graduating unit of the apparatus increases the atmospheric humidity without, for example, using spraying; a "natural" increase in the atmospheric humidity is present. All that is required is transportation and outdoor weathering with subsequent investigation in a dry hot climate (for example Arizona or the Kalahari), and the wet hot climate at least can be produced in the dry hot climate. Consequently, with one transport of test samples, in particular motor vehicles, for example to Arizona or into the Kalahari (dry hot climate), it is possible to investigate outdoor weathering both in an (unmodified) dry hot climate and, with the aid of the inventive apparatus for increasing the atmospheric humidity, for outdoor weathering in an (artificially influenced or produced) wet hot climate (for example, such as corresponds to that in Florida or the Kwazulu Natal). Furthermore, the device for measuring the level of the atmospheric humidity in the test area in conjunction with an appropriate recording of the measurement results in a statement being made as to which atmospheric humidity was present over time during the test period. It is therefore checked whether and when a wet hot climate is or was present. As mentioned, the test samples can, in particular, be motor vehicles; however, the test samples can also be any other type of samples for which it makes sense to conduct a test with regard to outdoor weathering (samples with (external) paints to be tested, coated (window) glasses, plastics for the external area etc.).

The inventors were the first to have established, surprisingly, that outdoor weathering in the wet hot climate in a dry hot climate zone can be readjusted "outdoors" without there being initiated aging processes that do not occur outdoors. In addition, substantial costs are spared, since samples of substantial dimension such as for example, motor vehicles, need be transported only to a location with a dry hot climate.

It is preferred for the apparatus to have control of the profile of the atmospheric humidity as a function of the distance from the graduating unit, in order to obtain defined, adjustable conditions in the test area. By controlling the profile of the atmospheric humidity as a function of distance from the graduating unit, it is possible to adapt a test area to the available surface by, for example, appropriately adjusting the atmospheric humidity when given a relatively large distance of a plurality of graduating units or of the wings of a graduating unit. It is likewise possible to take account of a short distance of graduating units or wings of a graduating unit from one another.

For a particularly simple configuration, the graduating unit comprises a plurality of wings forming a partially surrounded test area. Owing to the partially surrounded test area, a further increase in the atmospheric humidity in the test area is possible, since an even more saturated atmosphere can be produced with the aid of vapor and aerosols of the liquid. The atmospheric humidity is increased on a plurality of sides when a test area is formed that is partially surrounded.

The graduating unit preferably has two juxtaposed trickling surfaces that enclose an angle. It is hereby possible to set the irradiation angle with reference to the atmospheric humidity from the graduating unit, in order to obtain a further defined possibility of evaporation with regard to the liquid.

The graduating unit preferably has a trickling surface that is formed from a branched framework. It is hereby possible to use materials that are available or present on site, in order to obtain a trickling surface with increased surface, in order to raise the efficiency of the graduating unit with reference to the increase in atmospheric humidity. The branched framework is stable and supplies a large surface with cavities.

It is preferred to use as liquid water that is present on site. With water as liquid, it is possible to adjust a wet hot climate by increasing the atmospheric humidity.

It is also preferably possible to make use as the liquid of saline water with the aid of which a wet hot climate with a saline atmosphere can be obtained.

In a preferred design, the graduating unit is designed as part of a sight screen around the test area so that with the increase in the atmospheric humidity it is also possible to provide protection as to whether and which test samples are present in the test area.

As further protection; the graduating unit can preferably be configured with an anti-climb screen on the side averted from the test area. The anti-climb screen can have barbed wire, for example.

In order to ensure a specific level of atmospheric humidity in the test area in a simplified way, it is possible to provide a controller that is connected to the device for measuring the level of atmospheric humidity. Automation can take place by virtue of the fact that the graduating unit provides irrigation, or a magnified irrigation upon undershooting of a minimum desired value.

For the purpose of simplified documentation and logging, a device for recording the measured level of atmospheric humidity can be provided by the device for measuring the level of the atmospheric humidity during the test period, which can be handed out to potential clients as a record. The logging can be present, or be produced, electronically or on paper.

Further configurations of the invention may be gathered from the following description and the subclaims.

The invention is explained in more detail below with the aid of an exemplary embodiment illustrated in the attached schematics:

Figure 1:
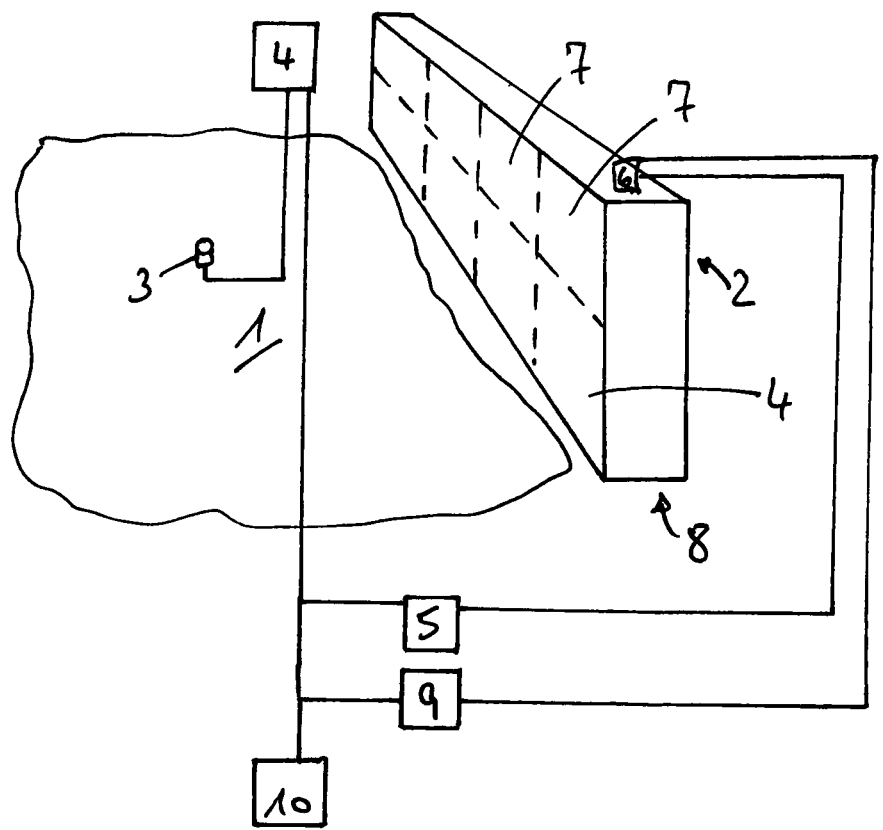
FIG. 1 shows a perspective schematic of an inventive apparatus for outdoor weathering.
Figure 2:
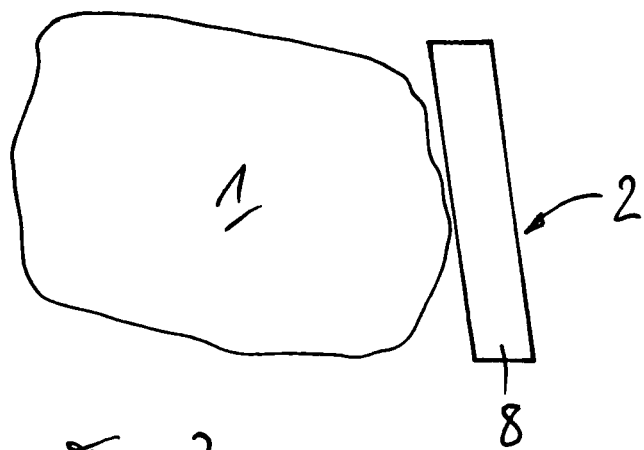
FIG. 2 shows a schematic of the apparatus for outdoor weathering in accordance with FIG. 1, in a plan view.

An inventive apparatus for increasing the atmospheric humidity for outdoor weathering, in particular of motor vehicles, is shown in FIG. 1 in a perspective schematic. A test area 1 is provided for setting up one or more samples to be tested, for example one or more motor vehicles.

The apparatus for increasing the atmospheric humidity of an outdoor weathering facility comprises a graduating unit 2 for controlling the level of the atmospheric humidity in the test area 1. The level of the atmospheric humidity is controlled by the discharge of an evaporated amount of liquid. Arranged in and/or on the test area 1 is a sensor 3 of a device 4 for measuring the level of the atmospheric humidity as a function of time during a test period. The device 4 for measuring the level of the atmospheric humidity can be used to provide a statement on the atmospheric humidity prevailing in the test area 1.

Furthermore, a controller 5 can be used to control the profile of the atmospheric humidity as a function of the distance from the graduating unit 2. The controller 5 can, for example, control an irrigation device 6 (comprising a pump with a pipeline or hose line system) of the graduating unit 2 so that more or less liquid trickles via trickling surfaces 7 of the graduating unit 2. The irrigation device 6 can apply a liquid from a reservoir to the graduating unit 2 from above so that the liquid trickles through the trickling surfaces 7 and natural evaporation is enabled by insolation and wind.

In order to control the profile of the atmospheric humidity as a function of the distance from the graduating unit 2, and initially to determine the profile, it is possible to provide a plurality of sensors at different distances from the graduating unit 2 that are respectively configured for measuring the atmospheric humidity. The sensors for measuring the profile of the atmospheric humidity as a function of the distance from the graduating unit 2 can be designed like the sensors 3.

Figure 3:
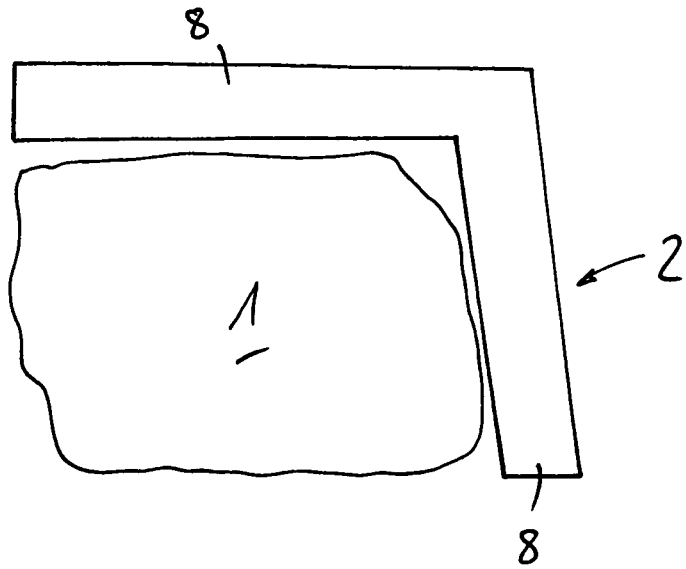
FIG. 3 shows a schematic of a second exemplary embodiment of the inventive apparatus for outdoor weathering, in a plan view.

FIG. 3 shows an exemplary embodiment of the apparatus for increasing the atmospheric humidity, in the case of which the graduating unit 2 comprises a plurality of wings 8 for forming a partially surrounded test area 1. The wings 8 of the graduating unit 2 form an "L" in plan view.

Figure 4:
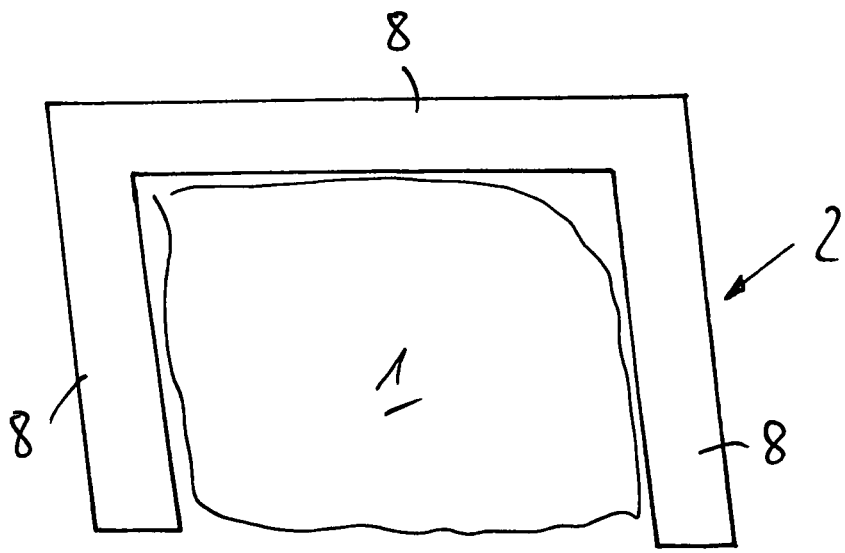
FIG. 4 shows a schematic of a third exemplary embodiment of the inventive apparatus for outdoor weathering, in a plan view.

FIG. 4 shows a further exemplary embodiment of the apparatus for increasing the atmospheric humidity in the case of which the wings 8 of the graduating unit 2 form a "U" in plan view.

Two juxtaposed trickling surfaces 7 that enclose an angle with one another can be provided for setting an angle of emission for the atmospheric humidity from the graduating unit 2.

To achieve a simplified design, the one or several trickling surfaces 7 of the graduating unit 2 is/are formed from a branched framework or bundle of branches, in order, to make use of materials that are present on site. A trickling surface 7 is obtained which has a raised surface that increases the efficiency of the graduating unit 2 with reference to the increase in the atmospheric humidity. The branched framework or the bundle of branches is stable and therefore delivers a large surface with cavities.

If water is used as the liquid for irrigating the trickling surfaces 7 of the graduating unit 2, it is possible to set a wet hot climate with the apparatus for increasing the atmospheric humidity. If saline water is used as the liquid for the irrigation of the trickling surfaces 7 of the graduating unit 2, it is possible to set a wet hot climate with a saline atmosphere.

The graduating unit 2 can be designed as part of a sight screen, and/or have an anti-climb screen.

A controller 9 is provided that is connected to the device 4 for measuring the level of the atmospheric humidity. The controller 9 is configured such that the controller 9 initiates a magnified irrigation of the graduating unit 2 with liquid in the event of the undershooting of a minimum desired value for the measured atmospheric humidity. The controller 9 acts on the irrigation device 6 to the effect that a larger amount of liquid is applied to the trickling surfaces 7 of the graduating unit 2. It can also be provided that the controllers 5 and 9 are combined in one controller that is, for example, configured as a microcontroller or an analog circuit.

Furthermore, provided in the exemplary embodiments illustrated is a device 10 for recording the measured level of the atmospheric humidity that records the measured atmospheric humidity during the test period. In this case, a continuous log may be kept, or measured values can be recorded at prescribed time intervals, for example once per hour or per day. Paper or an electronic medium can serve as recording medium.

The invention claimed is:

1. An apparatus for increasing the atmospheric humidity of an outdoor weathering facility of test samples in a test area having a graduating unit for controlling the level of the atmospheric humidity in the test area by discharging an evaporated amount of liquid, and having a device for measuring the level of the atmospheric humidity as a function of the time during a test period, and wherein the graduating unit comprises a plurality of wings for forming a partially surrounded test area.

2. The apparatus as claimed in claim 1, having control of a profile of the atmospheric humidity as a function of the distance from the graduating unit.

3. The apparatus as claimed in claim 1, in which water can be used as liquid.

4. The apparatus as claimed in claim 3, in which the water is saline.

5. The apparatus as claimed in claim 1, in which there is provided a controller that is connected to the device for measuring the level of atmospheric humidity and that is configured for irrigating the graduating unit with liquid upon overshooting of a minimum value for the measurement of atmospheric humidity.

6. The apparatus as claimed in claim 1, in which a device is provided for recording the measured level of the atmospheric humidity during the test period.

7. An apparatus for increasing the atmospheric humidity of an outdoor weathering facility of test samples in a test area having a graduating unit for controlling the level of the atmospheric humidity in the test area by discharging an evaporated amount of liquid, and having a device for measuring the level of the atmospheric humidity as a function of the time during a test period, and wherein the graduating unit has two juxtaposed trickling surfaces that enclose an angle.

8. An apparatus for increasing the atmospheric humidity of an outdoor weathering facility of test samples in a test area having a graduating unit for controlling the level of the atmospheric humidity in the test area by discharging an evaporated amount of liquid, and having a device for measuring the level of the atmospheric humidity as a function of the time during a test period, and wherein the graduating unit has a trickling surface that is formed as a branched framework.

9. An apparatus for increasing the atmospheric humidity of an outdoor weathering facility of test samples in a test area having a graduating unit for controlling the level of the atmospheric humidity in the test area by discharging an evaporated amount of liquid, and having a device for measuring the level of the atmospheric humidity as a function of the time during a test period, and wherein the graduating unit is designed as part of a sight screen around the test area.

10. An apparatus for increasing the atmospheric humidity of an outdoor weathering facility of test samples in a test area having a graduating unit for controlling the level of the atmospheric humidity in the test area by discharging an evaporated amount of liquid, and having a device for measuring the level of the atmospheric humidity as a function of the time during a test period, and wherein the graduating unit is configured with an anti-climb screen.

* * * * *